(12) United States Patent
Avidano et al.

(10) Patent No.: US 11,523,850 B2
(45) Date of Patent: Dec. 13, 2022

(54) MODULAR SPINAL SCREW YOKE INSERTER

(71) Applicant: SPINE WAVE, INC., Shelton, CT (US)

(72) Inventors: Eugene Avidano, Stratford, CT (US); Dylan Freund, San Marcos, CA (US); Mark Serokosz, New Fairfield, CT (US); Andrea Wright, Wallingford, CT (US)

(73) Assignee: SPINE WAVE, INC., Shelton, CT (US)

( * ) Notice: Subject to any disclaimer, the term of this patent is extended or adjusted under 35 U.S.C. 154(b) by 283 days.

(21) Appl. No.: 16/882,855

(22) Filed: May 26, 2020

(65) Prior Publication Data

US 2020/0375638 A1 Dec. 3, 2020

Related U.S. Application Data

(60) Provisional application No. 62/853,831, filed on May 29, 2019.

(51) Int. Cl.
*A61B 17/70* (2006.01)
*A61B 17/00* (2006.01)
(52) U.S. Cl.
CPC .............. *A61B 17/7082* (2013.01); *A61B 2017/00367* (2013.01)

(58) Field of Classification Search
CPC ............ A61B 17/7076; A61B 17/7077; A61B 17/708; A61B 17/7082; A61B 17/7091; A61B 2017/00367; A61B 2017/00389; A61B 2017/00393
USPC ......................................... 606/99, 104, 86 A
See application file for complete search history.

(56) References Cited

U.S. PATENT DOCUMENTS 8,876,869 B1 11/2014 Schafer et al.
9,615,862 B1 * 4/2017 Doubler ............. A61B 17/7076

* cited by examiner

*Primary Examiner* — Eduardo C Robert
*Assistant Examiner* — Christina Negrellirodriguez
(74) *Attorney, Agent, or Firm* — Hoffmann & Baron, LLP

(57) ABSTRACT

An inserter for attaching a modular yoke to a bone screw and for providing an indication of attachment, comprises a tubular body having a central lumen, distal and proximal ends, and an attachment portion for releasable attachment to a yoke having a bottom opening for receipt of a head of said bone screw. The inserter includes an inner shaft having a distal end configured to be received into the yoke, the shaft being axially movable within the lumen from first to second axial positions in response to the introduction of the bone screw head into the yoke bottom opening. An indicator button supported by the body is movable in response to axial movement of the shaft from a first indicator position indicating the first axial position of the shaft relative to the body to a second indicator position indicating the second axial position of the shaft relative to the body.

23 Claims, 7 Drawing Sheets

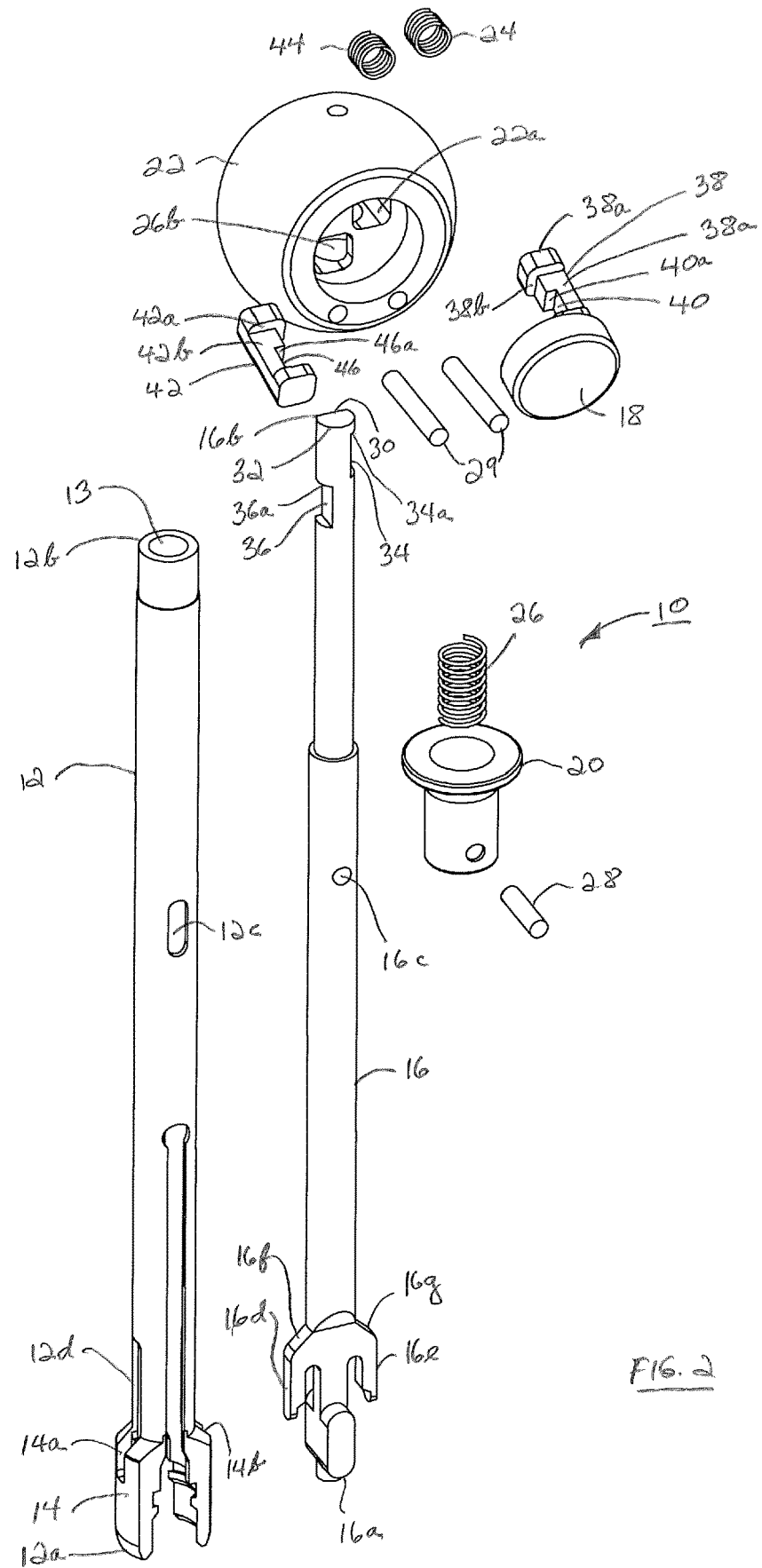

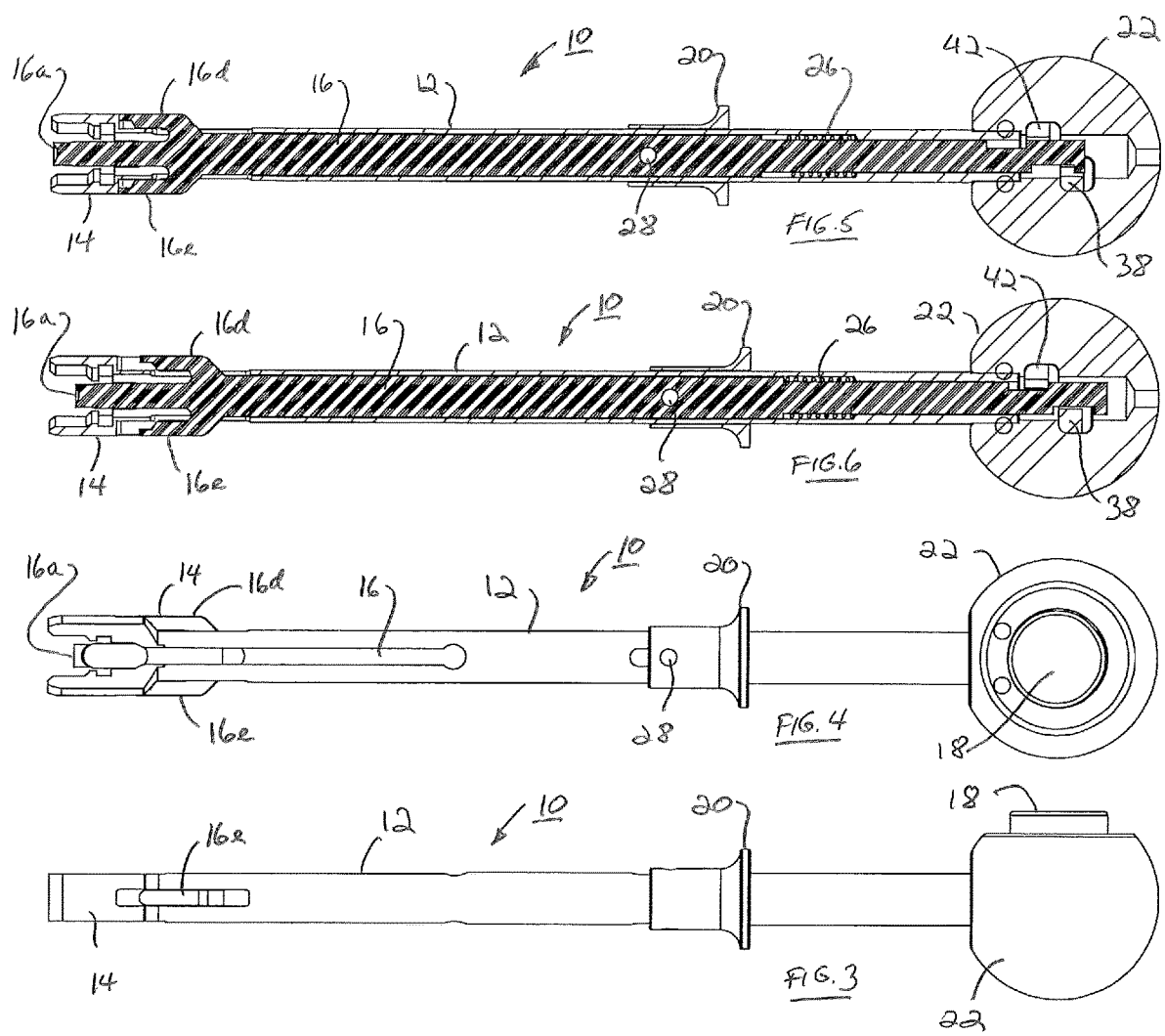

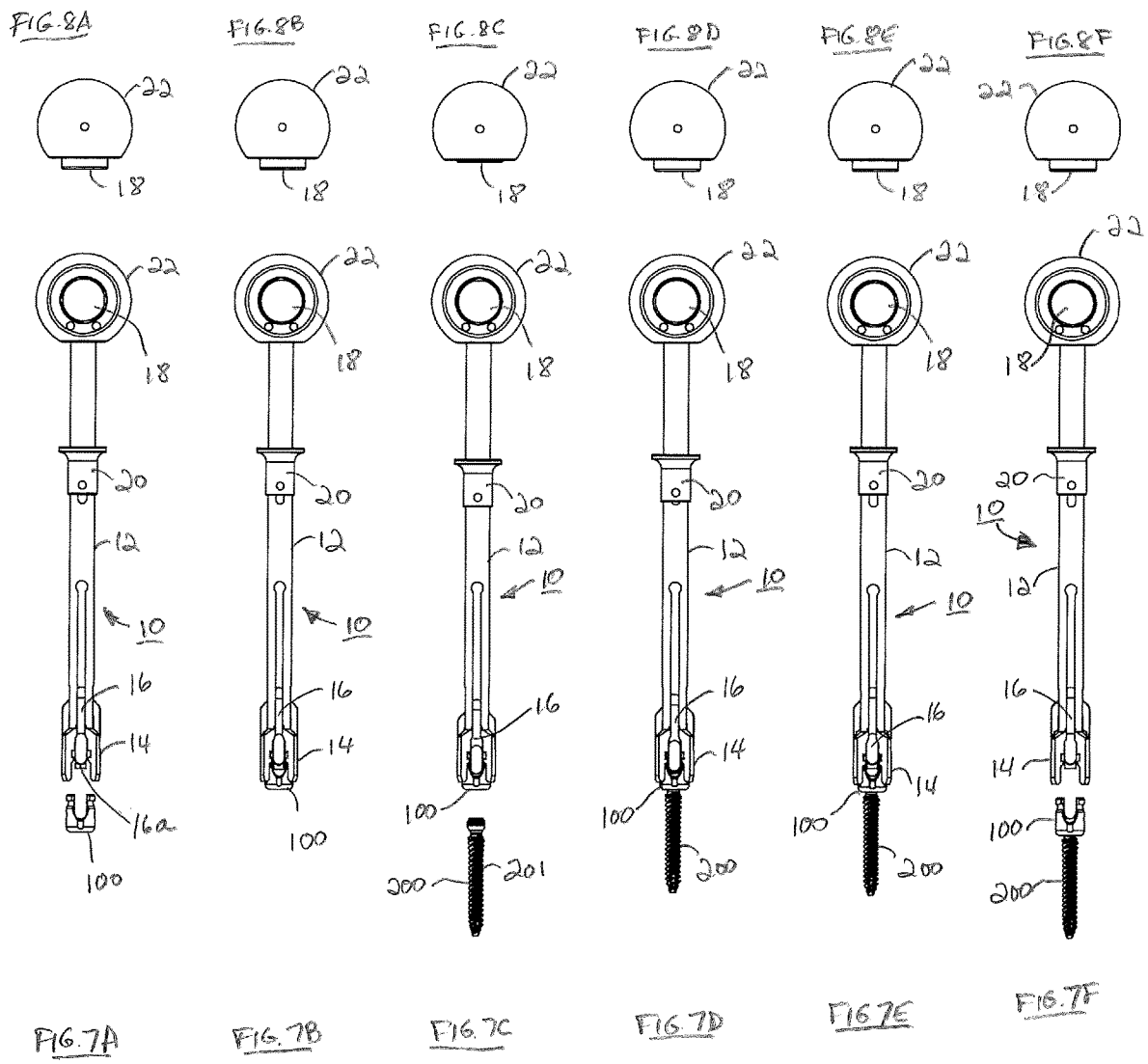

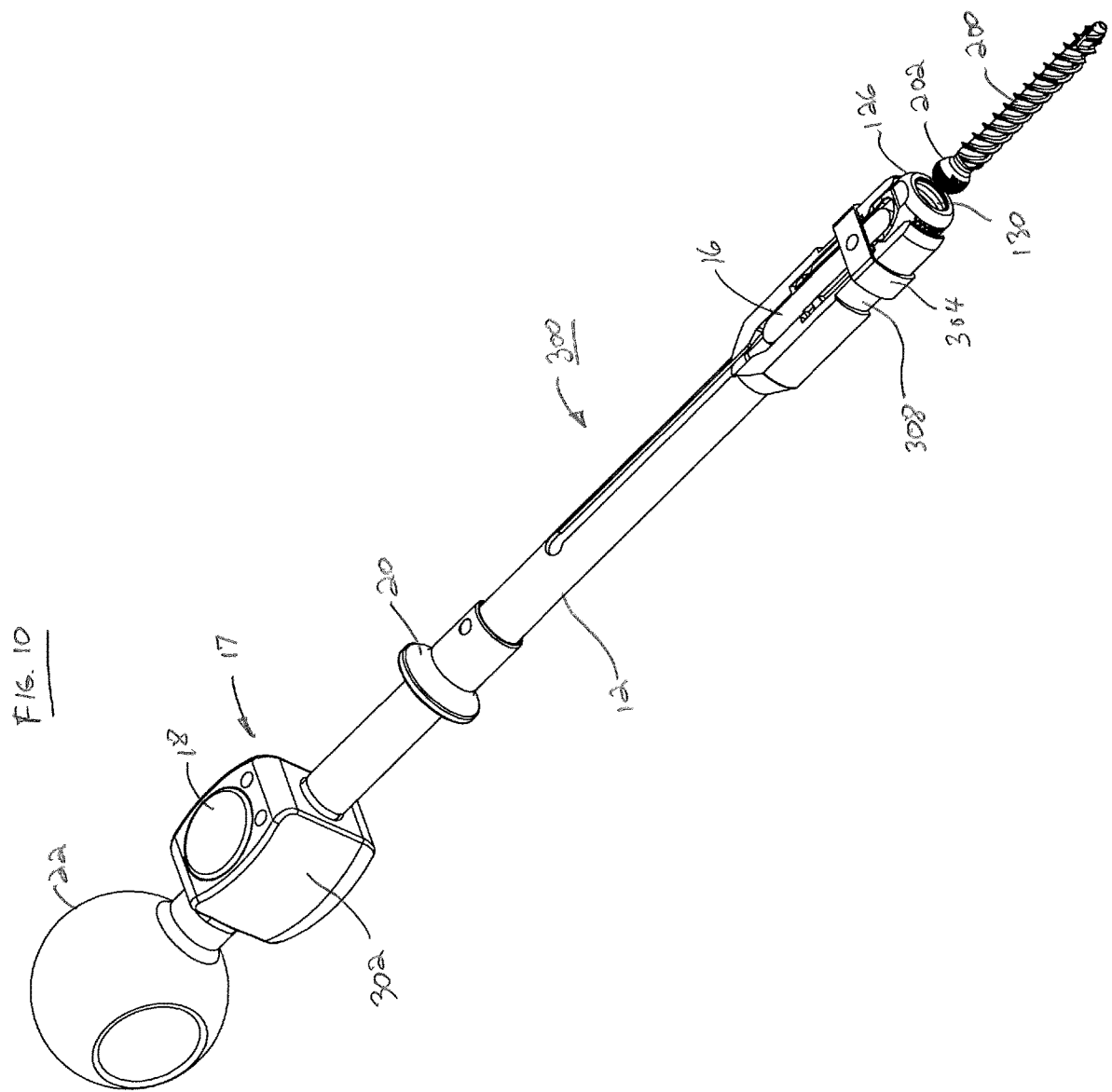

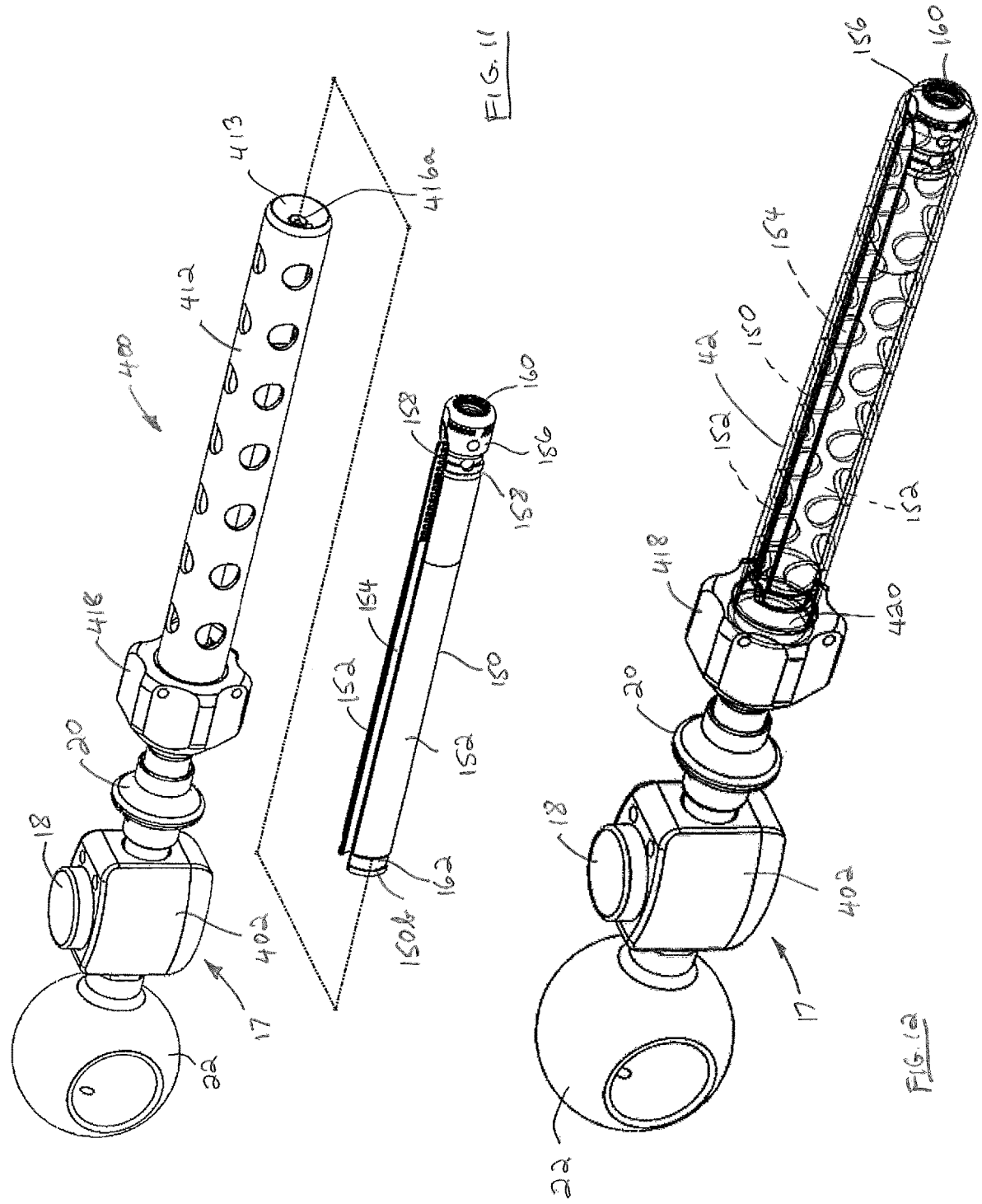

MODULAR SPINAL SCREW YOKE INSERTER

CROSS-REFERENCE TO RELATED APPLICATION

This application claims the benefit of U.S. Provisional Patent Application No. 62/853,831, filed May 29, 2019, the entire contents of which are incorporated by reference herein.

FIELD OF THE INVENTION

The subject invention relates to a surgical instrument, and more particularly to an inserter that is used to attach a modular yoke to a spinal screw during surgery and to provide an indication that the yoke is securely attached to the screw.

BACKGROUND OF THE INVENTION

Traditional polyaxial pedicle screws comprise an elongate shaft threaded at one end and a head, typically having a spherical surface, at the other end. A yoke having a U-shaped channel for receiving a spinal fixation rod is typically pre-assembled to the screw head in a manner to allow articulating movement of the yoke relative to the threaded shaft. In a modular pedicle screw construction, the yoke is configured to be articulatingly attached to the screw head in situ subsequent to the threaded installation of the threaded shaft into a pedicle. Certain efforts have been made to provide modular tensioned pedicle screws wherein the modular yoke may be attached to the spherical head of the pedicle screw by an inserter to hold and properly attach the yoke to a screw in situ after threaded installation into a pedicle of a vertebral body. One example of such an inserter is shown and described in U.S. Pat. No. 8,876,869, entitled "Polyaxial Bone Screw Assembly", issued on Nov. 4, 2014 to Schafer et al. (the '869 patent). The inserter disclosed in the '869 patent is described as having the capability to test the attachment of the yoke to the bone screw so as to verify that the yoke is securely attached.

Nevertheless, there is a desire for an inserter for use in attaching a modular yoke to a bone screw that is easy to use and provides an indication that the yoke is properly attached to the bone screw.

SUMMARY OF THE INVENTION

It is an object of the invention to provide an inserter to attach a modular yoke to a head of bone screw, such as a pedicle screw. It is a further object of the invention to provide an inserter that will provide an indication that the modular yoke is properly attached to the head of the bone screw.

BRIEF DESCRIPTION OF THE DRAWING FIGURES

FIG. 2 is a perspective exploded view of the inserter of FIG. 1

FIGS. 3 and 4 are side elevation and top plan views of the inserter of FIG. 1.

FIG. 5 is a longitudinal cross-sectional view of the inserter as seen along viewing lines V-V of FIG. 3 showing an inner shaft of the inserter in a first position.

FIG. 6 is the longitudinal cross-sectional view of the inserter of FIG. 5 with the inner shaft of the inserter moved to a second position.

FIGS. 7A-7F are a series of side elevation views of the inserter of FIG. 1 showing the sequence of operational attachment of a yoke to a bone screw by the inserter.

FIGS. 8A-8F are a series of side elevation views of the handle of the inserter of FIG. 1, coinciding with the views of FIGS. 7A-7F and illustrating the position of the indicator button in each of the respective sequences.

FIG. 10 is a perspective view of the inserter of FIG. 9 shown holding the reduction screw modular yoke with the bone screw shown spaced therefrom.

FIG. 11 is a perspective view of an inserter in accordance with a further arrangement for attaching an extended tab modular yoke to a bone screw, the extended tab modular yoke shown spaced from the inserter.

FIG. 12 is a perspective view of the inserter of FIG. 11 with the extended tab modular yoke attached to the inserter.

DETAILED DESCRIPTION OF THE EMBODIMENTS

Figure 1:
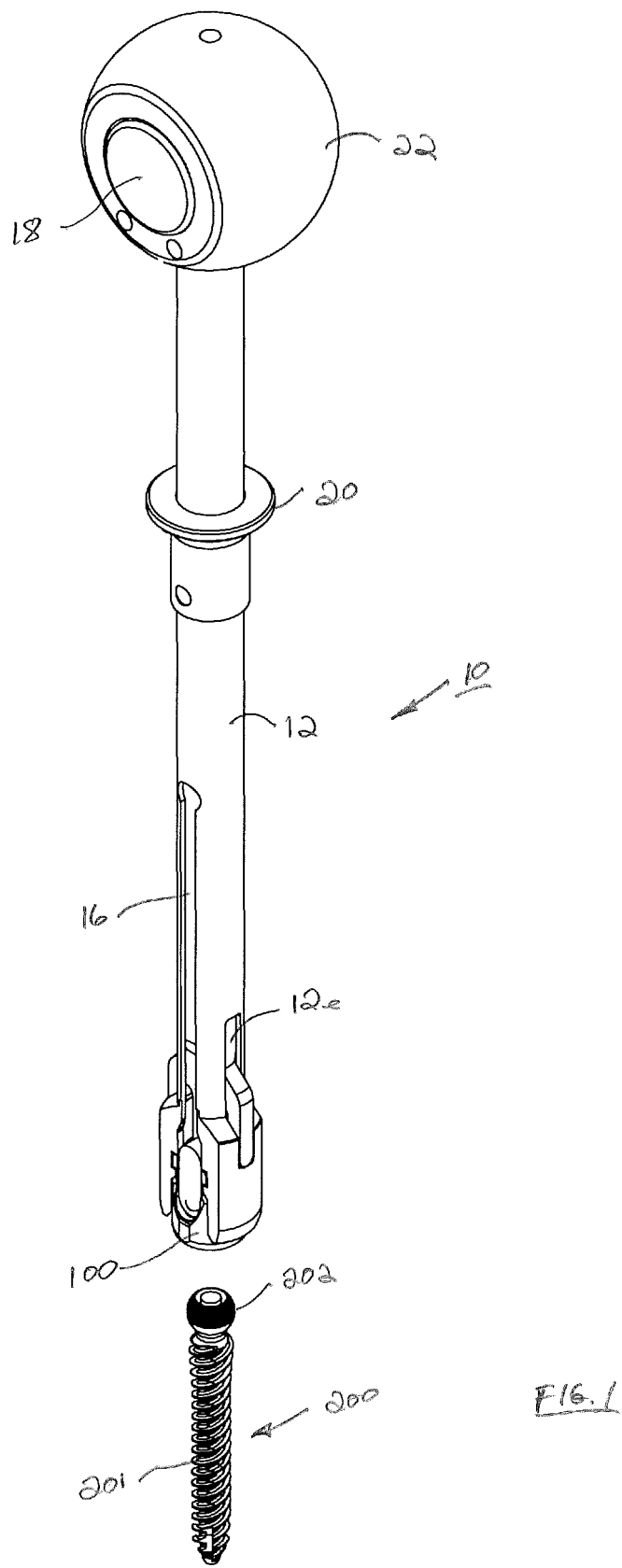
FIG. 1 is a perspective view of an inserter holding a modular yoke for attachment to a bone screw shown spaced from the inserter in accordance with one arrangement of the present invention

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

The present invention has particular facility in a spinal fixation system that spans between successive vertebrae of the spine. An elongated member, such as a connecting rod that extends along a length of the spine, provides an anchor point for connecting each vertebra to the system. The rod, typically formed of stainless steel, is contoured by bending to approximate the normal curvature of the spine for the particular instrumented spinal segments. An anchor device is provided for connecting each of the vertebral segments to the rod. These anchor devices may include hooks, bolts, screws or other means for engaging a vertebra. For the purposes of the present invention, the spinal anchor device is a polyaxial bone screw. More specifically, the polyaxial bone screw is a modular tensioned polyaxial pedicle screw. In a particular example, modular tensioned pedicle screw is configured and sized for connection to the thoraco-lumbar region of the spine from the posterior direction for threaded engagement with a pedicle of a vertebra. Configurations for use in other regions of the spine and from other directions are also contemplated. Further details of a modular tensioned screw are described in commonly owned U.S. patent application Ser. No. 16/843,160, entitled "Modular Tensioned Spinal Screw", filed Apr. 8, 2020 by Eugene Avidano et al. ("the '160 application"), the entire contents of which are incorporated herein by reference.

A modular spinal screw yoke inserter 10 as shown in FIG. 1 is provided to hold and attach a modular yoke 100 to a bone screw 200, such as a pedicle screw. Upon attachment, modular yoke 100 and bone screw 200 form a modular polyaxial screw. In a particular arrangement, yoke 100 is formed to be attached to screw 200 to articulate thereon and may be tensioned in a manner as described in the '160 application. Bone screw 200 may be of conventional configuration comprising an elongate threaded shank 201 and a head 202 having a spherical surface.

Referring now to FIGS. 2-6, details of inserter 10 are described. Inserter 10 includes a main body 12 that is tubular and has a distal end 12a and a proximal end 12b, with a central lumen 13 extending therethrough. Main body 12 has an attachment portion 14 that is configured for holding the yoke 100. In the arrangement shown in FIG. 2, attachment portion 14 is defined by an expandable and contractable tip 14 at the distal end 12a An elongate inner shaft 16, axially movable within central lumen 13 of main body 12, has a distal end 16a and a proximal end 16b. As will be described, distal movement of inner shaft 16 within main body 12 locks the distal tip 14 to hold the yoke 100 in position. Proximal movement of inner shaft 16 actuates an indicator mechanism 17 when the yoke 100 is properly attached onto screw 200 and expands the distal tip 14 for receipt of yoke 100. A plunger 20 is connected to inner shaft 16 and is used to actuate inner shaft 16 to release the yoke 100 after it has been assembled to screw 200.

A spherical handle 22 attached to the proximal end 12b of the main body 12 houses indicator mechanism 17 as well as provides a surface to grip inserter 10. Indicator mechanism 17 includes an indicator button 18 that is configured to pop out exteriorly from handle 22 under the bias of a spring 24 when the inner shaft 16 is moved proximally to the correct height indicating that the yoke 100 has been successfully placed on the screw 200. Indicator button 18 may also be depressed into handle 22 to move inner shaft 16 proximally, as will be described. A second spring 26 holds the inner shaft 16 at a secondary location, keeping the distal tip 14 connected to the yoke 100 after the indicator button 18 actuates. Tension on the secondary spring 26 is overcome when the inner shaft 16 is manually pulled proximally via the plunger 20 to release the assemble yoke 100. The plunger 20 is attached to inner shaft 16 at opening 16c by a pin member 28 which slides within a slot 12c formed in main body 12. Movement of the inner shaft 16 proximally expands the inserter tip 14 in order to remove yoke 100 from screw 200 or accept another yoke 100.

Distal end 16a of inner shaft 16 is configured to enter into a U-shaped channel formed between opposing arms of yoke 100 that is provided for receiving a spinal fixation rod. A pair of opposed locking wings 16d and 16e are included on inner shaft 16 adjacent to distal end 16a for movement with inner shaft 16. In Locking wings 16d and 16e are configured to extend through opposing elongated slots 12d and 12e (FIG. 1) that are formed through main body 12 and to slide therein upon axial movement of inner shaft 16. Locking wings 16d and 16e include inclined surfaces 16f and 16g on their respective upper proximal ends a shown in FIG. 2. As inner shaft 16 is moved proximally, inclined surfaces 16f and 16g engage main body 12 at the upper ends respectively of slots 12d and 12e to expand distal tip 14 for receipt of yoke 100. As inner shaft 16 is moved distally, locking wings 16d and 16e will engage exterior grooves 14a and 14b in distal tip 14 to hold yoke 100 in position with distal end 16a for attachment to head 202 of screw 200, as will be described.

Proximal end 16b of inner shaft 16 as shown in the exploded view of FIG. 2 is formed to have a generally D-shaped configuration defined by a flat surface 30 and an outer curved surface 32. Proximal end 16b further includes two recessed locking surfaces 34 and 36 that are diametrically opposite and axially spaced from each other, with recessed locking surface 36 being located more distally than recessed locking surface 34. Projecting outwardly transversely from indicator button 18 is an elongate post 38 which includes a recessed locking surface 40. One end (not shown) of post 38 is attached to indicator button 18 such that post 38 and indicator button 18 move jointly. The opposing end 38a of post 38 is received in a first opening 22a formed in handle 22. Elongate post 38 and thereby indicator button 18 are slidably supported within opening 22a by handle 22 under the bias of a spring 24 for movement in a direction transverse to the axial direction of inner shaft 16. A second elongate post member 42 is movably supported by handle 22 within an opening 22b formed in handle 22 under the bias of a spring 44. Elongate post 42 is movable in a direction transverse to the axial direction of inner shaft 16 independently of elongate post 38. However, depression of indicator button 18 inwardly moves both elongate post 38 and elongate post 42. Handle 22 is suitably attached to main body 12 by a pair of pins 29.

In order to operate the yoke inserter 10, a user pulls plunger 20 and thereby inner shaft 16 from the position shown in FIG. 5 toward the proximal end of the inserter 10 to the position shown in FIGS. 6, 7A and 8A expanding distal tip 14 of the inserter and deploying the indicator button 18 in the out position. The distal opening of the yoke inserter 10 is then aligned with the slot of the yoke 100 and the expanded tip 14 of the inserter 10 is placed over the top of the yoke 100 as the distal end 16a of inner shaft 16 enters the slot of yoke 100, as shown in FIG. 7B. With yoke 100 fully seated into the inserter 10 indicator button 18 is then fully depressed into the handle 22 as shown in FIG. 7C. An audible click will be heard as the inner shaft 16 slides distally downwards locking the inserter 10 onto the yoke 100 as shown in FIG. 7C. The button 18 will be retained in the depressed state. The inserter 10 with attached yoke 100 are now ready to be assembled to screw 200.

To assemble yoke 100 held by inserter 10, an opening 102 in the bottom of the yoke 100 is placed over the head 202 of the screw 200 as shown in FIG. 7D and inserter 10 is then pushed distally downwards relative to yoke 100 causing inner shaft 16 to move proximally upwards. When inner shaft 16 moves up proximally far enough so that transverse surface 40a of recess 40 clears recess 34 of inner shaft 16 indicator button 18 will pop outwardly under the bias of spring 24. At this point, transverse surface 38b of elongate post 38 is in contact with flat surface 30 of inner shaft 16. In this position with indicator button 18 deployed outwardly inner shaft 16 is prevented from moving distally downwardly due to the top proximal surface 34a of recess 34 resting on an upper proximal surface 38c of elongate post 38. Once the screw 200 is attached to the yoke 100, the head 202 of screw 200, or a component within the yoke 100 in response to insertion of the head 202 of screw 200, will contact distal end 16a of inner shaft 16 of inserter 10 pushing inner shaft 16 proximally toward handle 22 and triggering an audible click as indicator button 18 pops outwardly from handle 22 as shown in FIG. 8D. This will indicate that screw 200 has moved into the yoke 100 far enough for a proper assembly. At this point the operator can reset the instrument to double check that screw 200 has been properly assembled to yoke 100 by depressing indicator button 18 to cause inner shaft 16 to move downwardly. With the inserter 10 reset the operator can now push downwards until the indicator button 18 is again moved outwardly providing both a visual and audible indication of the axial position of inner shaft 16.

To remove the yoke inserter 10 from the assembled yoke 100 and screw 200 the user will pull plunger 20 proximally toward handle 22 as shown in FIGS. 7E and 8E causing inner shaft 16 attached to plunger 20 by pin 28 to likewise move proximally. Such movement of inner shaft 16 will cause the expandable tip 14 of main body 12 to spread until the yoke 100 has been released. Another audible click will be heard as distal tip 14 expands and the inserter 10 can be removed from the assembled screw as shown in FIGS. 7F and 8F. When inner shaft 16 moves up proximally far enough so that transverse surface 46a of recess 46 on elongate post 42 clears recess 36 of inner shaft 16 elongate post 42 will move transversely under the bias of spring 44 until transverse surface 42a of elongate post 42 is in contact with the flat surface 30 of inner shaft 16. After elongate post 42 has so moved outwardly inner shaft 16 is prevented from moving downwardly due to the top surface 36a of recess 36 resting on an upper proximal surface 42b of elongate post 42. This is the loading position at which yoke inserter 10 can snap onto a new un-assembled yoke 100, as depicted in FIG. 6. Once the yoke 100 is held by the expandable tip 14 of main body 12 the indicator button 18 can be depressed to reset the inserter for use.

It should now be appreciated that inserter 10 may be used to hold a yoke 100 during the screw assembly process as well as to indicate when the screw yoke 100 has been successfully attached to the screw 200. The indication is visual, audible and tactile. After the screw is assembled and indicated the inserter would remain attached to the assembled yoke and screw. The indicator button 18 may be reset and tested again on an assembled yoke and screw. While the inserter 10 has been described herein as particularly useful to assemble a tensioned modular yoke in situ to a screw previously installed in a surgical site, it should be understood that the inserter 10 may also be used to assemble a modular yoke that does not have tensioning features. In addition, inserter 10 may also be used to attach a modular yoke to the screw before the screw has been placed in the patient's body.

In addition, it should be appreciated that the yoke inserter 10 has a two-stage lock that will indicate when the yoke 100 is assembled to the screw 200 without disengaging from the yoke and screw assembly. This allows for additional testing by physically manipulating the inserter 10 and/or resetting the indicator button 18 and pressing down the inner shaft 16 to indicate the yoke is assembled correctly.

Figure 9:
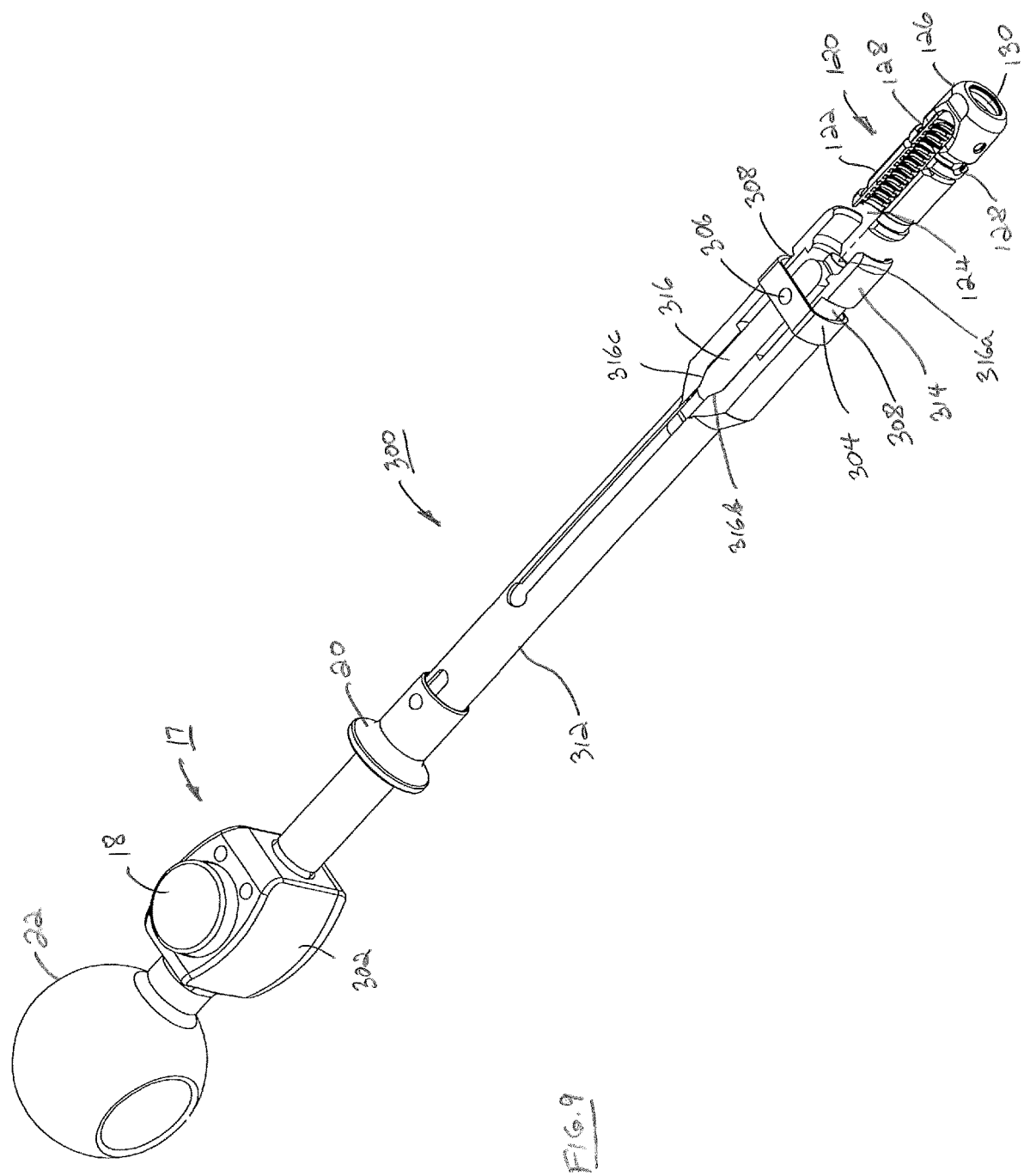
FIG. 9 is a perspective view of an inserter in accordance with another arrangement for attaching a reduction screw modular yoke to a bone screw, the reduction screw modular yoke shown spaced from the inserter.

While the inserter 10 has been illustrated and described in detail in the drawings and foregoing description, the same should be considered as illustrative and not restrictive in character. For example, while the yoke inserter 10 has been described herein as attaching traditional yoke 100 to a bone screw 200, it should be appreciated that an inserter within the scope of the invention may also be used to attach a modular yoke of other configurations to a bone screw. One such other example is shown in FIGS. 9-10 which illustrate an inserter 300 that is particularly configured to attach a reduction screw modular yoke 120 to a bone screw 200. This additional exemplary inserter 300 includes features that are common to inserter 10 described hereinabove and as such, those common features will have like reference numerals. In a particular arrangement, yoke 120 may be tensioned in a manner as described in the '160 application.

As depicted in FIG. 9, reduction screw modular yoke 120 includes a pair of spaced opposing arms 122 that together define a U-shaped channel 124 for receipt of a spinal rod. Arms 122 are attached to a yoke receiver 126 by frangible connectors 128 that may be broken to separate arms 122 from receiver 126 after proper seating of the spinal rod into the receiver 126. Receiver 126 as an opening 130 at its lower distal end for receipt of head 202 of bone screw 200. The additional length of arms 122 of reduction screw modular yoke 120 assists in the receipt of a spinal rod in surgery and for guiding the spinal rod down into receiver 126 for proper seating prior to being secured by a fastening screw.

Inserter 300 includes main body 312 that is tubular and has an attachment portion that is configured for holding the yoke 120. In the arrangement shown in FIG. 9, the attachment portion is defined by an expandable and contractable tip 314 at the distal end 312a. An elongate inner shaft 316 is axially movable within main body 312. Distal end 316a of inner shaft 316 is configured to enter into U-shaped channel 124 formed between opposing arms of yoke 100 that is provided for receiving a spinal fixation rod. Inner shaft 316 includes inclined surfaces 316b and 316c that engage main body 312 as inner shaft moves proximally to expand distal tip 314 for receipt of yoke 120.

A plunger 20 is connected to inner shaft 316 and is used to actuate inner shaft 316 to release the yoke 120 after it has been assembled to screw 200. A spherical handle 22 is attached to the proximal end of the main body 312 to provide a surface to grip inserter 300. Indicator mechanism 17, instead of being housed in handle 22 as is the case with inserter 10, is housed in a separate housing 302 adjacent handle 22. Indicator mechanism 17 is structurally the same as indicator mechanism 17 of inserter 10 and includes an indicator button 18 that is configured to pop out from housing 302 under the bias of spring 24 (not shown) when the inner shaft 316 is moved proximally to the correct height indicating that the yoke 120 has been successfully placed on the screw 200. A locking ring 304 is movably attached to inner shaft 316 by a pin 306. Locking ring 304 extends exteriorly around distal tip 314 and slides within a pair of opposite grooves 308 formed into the exterior surface of distal tip 314. Yoke 120 is configured to be received into distal tip 314 of inserter 300 as shown in FIG. 10. As inner shaft 316 is moved distally, locking ring 304 will slide distally in grooves 308 to the position shown in FIG. 10 to hold yoke 120 in position for attachment to head 202 of screw 200. The attachment of yoke 120 by inserter 300 to screw 200 and the actuation of indicator mechanism 17 is the same as that described above with respect to inserter 10.

Another such example of an inserter for use in attaching a modular yoke of another configuration to a bone screw is shown in FIGS. 11-12, which illustrate an inserter 400 that is particularly configured to attach an extended tab modular yoke 150 to a bone screw 200. This further exemplary inserter 400 also includes features that are common to inserter 10 described hereinabove and as such, those common features will have like reference numerals. In a particular arrangement, yoke 150 may be tensioned in a manner as described in the '160 application.

As depicted in FIG. 11, extended tab modular yoke 150 includes a pair of spaced opposing extended arms 152 that together define a U-shaped channel 154 for receipt of a spinal rod. Arms 152 are attached to a yoke receiver 156 by frangible connectors 158 that may be broken to separate arms 152 from receiver 156 after proper seating of the spinal rod into the receiver 156. Receiver 156 has an opening 160 at its lower distal end 150a for receipt of head 202 of bone screw 200. At the upper proximal end 150b, each arm includes a groove 162 for rotational attachment of modular yoke 150 to inserter 400, as will be described. The additional length of arms 152 of extended tab modular yoke 150 assists in the receipt of a spinal rod in surgery and for guiding the spinal rod down into receiver 156 for proper seating prior to being secured by a fastening screw. The length of arms 152 is configured such that during surgery proximal end 150b of yoke 150 extends exteriorly from the outer surface of the skin of a patient when yoke 150 is attached to a bone screw previously installed in a vertebral body of the patient. Such a construction allows use in minimally invasive spinal procedures wherein a separate individual incision may be provided for each bone screw.

Inserter 400 includes a tubular main body 412 and a knob 418 that has an internal attachment portion 420 configured for holding the yoke 150. In the arrangement shown in FIG. 12, attachment portion 420 is defined by an inner collar that has spaced flanges (not shown) for rotational engagement with grooves 162 of modular yoke 150 for attaching modular yoke 150 to inserter 400. Main body 412 has a central lumen 413 extending therethrough. An elongate inner shaft 416 is axially movable within lumen 413 of main body 412. Lumen 413 is dimensioned for receipt therein of modular body 150 such that inner shaft 416 extends into modular yoke 150 between arms 152 and distal end 416a resides in receiver 160 upon attachment of modular yoke 150 to main body 412. Distal movement of inner shaft 416 within main body 412 actuates an indicator mechanism 17 when the yoke 150 is properly attached onto a bone screw 200.

A plunger 20 is connected to inner shaft 316 and is used to actuate inner shaft 316 to release the yoke 150 after it has been assembled to screw 200. A spherical handle 22 is attached to the proximal end of the main body 412 to provides a surface to grip inserter 400. Indicator mechanism 17, instead of being housed in handle 22 as is the case with inserter 10, is housed in a separate housing 402 adjacent handle 22. Knob 418 and attachment portion 420 are rotatable relative to handle 22, housing 402 and inner shaft 416. Indicator mechanism 17 is structurally the same as indicator mechanism 17 of inserter 10 and includes an indicator button 18 that is configured to pop out from housing 402 under the bias of spring 24 (not shown) when the inner shaft 416 is moved proximally to the correct height indicating that the yoke 150 has been successfully placed on the screw 200.

The steps to attach yoke 150 by inserter 400 to screw 200 and the actuation of indicator mechanism 17 is similar as that described above with respect to inserter 10. Initially, the plunger 20 is pulled proximally and knob 418 is turned counterclockwise relative to handle 22 This causes indicator button 18 to pop out, indicating that inner shaft 416 is in its up (proximal) position. The extended arms 152 are inserted until they reach attachment portion 420 within knob 418. Knob 418 is then turned clockwise such the flanges of the inner collar slide into the grooves 162 on the proximal end of the extended arms 152, keeping them from moving proximally or distally and locking the extended arms 152 in place. Indicator button 18 is depressed by the user causing inner shaft 416 to move distally. The head 202 of bone screw 200 is introduced into opening 160 of yoke 150 causing inner shaft to move up (proximally) a sufficient distance to align inner shaft recesses 34 and 36 with post 38 and post member 42 respectively, thereby allowing springs 24 and 44 to push indicator button out from housing 402. This indicates that yoke 150 has been successfully attached to bone screw 200.

While the invention has been illustrated and described in detail in the drawings and foregoing description, the same should be considered as illustrative and not restrictive in character. As such, it is understood that only the preferred embodiments have been presented and that all changes, modifications and further applications that come within the spirit of the invention are desired to be protected.

What is claimed is:

1. An inserter for attaching a modular yoke to a bone screw and for providing an indication of attachment, comprising:
    a tubular body having a central lumen, a distal end, a proximal end, and an attachment portion for releasable attachment to the yoke having a bottom opening for receipt of a head of said bone screw;
    an elongate inner shaft having a distal end and a proximal end, said distal end of the elongate inner shaft including a portion configured to be received into said yoke, said inner shaft being axially movable within said central lumen from a first axial position to a second axial position in response to the introduction of the head of said bone screw into the bottom opening of said yoke; and
    an indicator button supported by said tubular body and movable automatically relative to said tubular body in response to axial movement of said inner shaft from a first indicator position indicating the first axial position of said inner shaft relative to said tubular body to a second indicator position indicating the second axial position of said inner shaft relative to said tubular body.

2. The inserter of claim 1, wherein the distal end of said inner shaft in said first axial position is disposed adjacent the distal end of said tubular body.

3. The inserter of claim 2, wherein the distal end of said inner shaft in said second axial position is disposed proximally of the distal end of said tubular body.

4. The inserter of claim 3, wherein said distal end portion of said inner shaft is configured to be responsive to movement of the head of said bone screw proximally into said yoke to move said inner shaft from said first axial position to said second axial position.

5. The inserter of claim 1, wherein said indicator button is depressible and biased to said second indicator position under the influence of a spring supported by said tubular body.

6. The inserter of claim 5, wherein said tubular body includes a handle adjacent the proximal end of said tubular body, said indicator button being movably supported by said handle.

7. The inserter of claim 6, wherein said indicator button includes an outer surface that is disposed in a depressed condition substantially within said handle when said indicator button is in the first indicator position.

8. The inserter of claim 7, wherein the outer surface of said indicator button is disposed exteriorly beyond said outer surface of said handle when said indicator button is in the second indicator position.

9. The inserter of claim 8, wherein automatic movement of said indicator button from said depressed condition in said first indicator position to said second indicator position causes an audible click.

10. The inserter of claim 9, wherein said indicator button is manually movable against a bias of said spring from said second indicator position to said first indicator position causing distal axial movement of said inner shaft to said first axial position.

11. The inserter of claim 1, wherein said attachment portion is defined by an expandable and contractable tip, and wherein movement of said inner shaft proximally relative to said tubular body causes the expandable and contractable tip at the distal end of said tubular body to expand.

12. The inserter of claim 11, wherein movement of said inner shaft distally relative to said tubular body causes the expandable and contractable tip to contract so as to lock said tubular body to said yoke.

13. The inserter of claim 12, further including a locking member movable with the axial movement of said inner shaft to engage an exterior surface of said expandable and contractable tip to lock said tubular body to said yoke.

14. The inserter of claim 1, wherein said attachment portion is defined by a surface on said tubular body that is configured to rotatably attach said tubular body to said yoke.

15. The inserter of claim 14, wherein said attachment portion is disposed between said indicator button and said distal end of said tubular body.

16. An inserter for attaching a modular yoke to a bone screw and for providing an indication of attachment, comprising:
a tubular body having a central lumen, a distal end, a proximal end, and an attachment portion for releasable attachment to the yoke having a bottom opening for receipt of a head of said bone screw;
an elongate inner shaft having a distal end and a proximal end, said distal end of the elongate inner shaft including a portion configured to be received into said yoke, said inner shaft being axially movable within said central lumen from a first axial position to a second axial position in response to the introduction of the head of said bone screw into the bottom opening of said yoke;
an indicator button supported by said tubular body and movable relative to said tubular body in response to axial movement of said inner shaft from a first indicator position indicating the first axial position of said inner shaft relative to said tubular body to a second indicator position indicating the second axial position of said inner shaft relative to said tubular body; and
a releasable first lock configured to prevent said inner shaft in said first axial position from moving distally, wherein said releasable first lock comprises a first locking surface on said indicator button and a first cooperative locking surface on said inner shaft, said first locking surface and said first cooperative locking surface being selectively engageable in response to movement of said indicator button.

17. The inserter of claim 16, further comprising a releasable second lock configured to prevent said inner shaft in said second axial position from moving distally.

18. The inserter of claim 17, wherein said releasable second lock comprises a second locking surface on a movable post supported by said tubular body and a second cooperative locking surface on said inner shaft, said second cooperative locking surface being axially spaced from said first cooperative locking surface, said second locking surface and said second cooperative locking surface being selectively engageable in response to movement of said indicator button.

19. An inserter for attaching a modular yoke to a bone screw and for providing an indication of attachment, comprising:
a tubular body having a central lumen, a distal end, a proximal end, and an attachment portion for releasable attachment to the yoke having a bottom opening for receipt of a head of said bone screw;
an elongate inner shaft having a distal end and a proximal end, said distal end of the elongate inner shaft including a portion configured to be received into said yoke, said inner shaft being axially movable within said central lumen from a first axial position to a second axial position in response to the introduction of the head of said bone screw into the bottom opening of said yoke;
an indicator button supported by said tubular body and movable relative to said tubular body in response to axial movement of said inner shaft from a first indicator position indicating the first axial position of said inner shaft relative to said tubular body to a second indicator position indicating the second axial position of said inner shaft relative to said tubular body;
a spring member supported by said tubular body, said spring member being configured to bias said inner shaft distally relative to said tubular body; and
a plunger connected to said inner shaft, said plunger being configured to manually move said inner shaft proximally against the bias of said spring member.

20. An inserter for attaching a modular yoke to a bone screw and for providing an indication of attachment, comprising:
a tubular body having a central lumen, a distal end and a proximal end, the distal end and an attachment portion for releasable attachment to the yoke having a bottom opening for receipt of a head of said bone screw;
an elongate inner shaft having a distal end and a proximal end, said distal end including a portion configured to be received into said yoke, said inner shaft being axially movable within said central lumen from a first axial position to a second axial position in response to the introduction of the head of said bone screw into the bottom opening of said yoke; and
an indicator mechanism supported by said tubular body and comprising an indicator button automatically movable relative to said tubular body from a first indicator position to a second indicator position in response to axial movement of said inner shaft toward the proximal end of said tubular body from said first axial position to said second axial position, said inner shaft being movable toward the distal end of said tubular body from said second axial position to said first axial position in response to manual movement of said indicator button from said second indicator position to said first indicator position.

21. The inserter of claim 20, wherein movement of said indicator button relative to said tubular body provides a visual indication of the axial position of inner shaft relative to said tubular body.

22. The inserter of claim 20, wherein movement of said indicator button relative to said tubular body provides an audible indication of the axial position of inner shaft relative to said tubular body.

23. The inserter of claim 20, wherein movement of said indicator button relative to said tubular body provides a tactile indication of the axial position of inner shaft relative to said tubular body.

* * * * *